(12) United States Patent
Motamedi

(10) Patent No.: US 11,244,131 B2
(45) Date of Patent: Feb. 8, 2022

(54) METHOD AND SYSTEM FOR EMERGENCY DATA RETRIEVAL FROM TWO DIMENSIONAL CODE

(71) Applicant: Marcus Sassan Motamedi, Joshua Tree, CA (US)

(72) Inventor: Marcus Sassan Motamedi, Joshua Tree, CA (US)

( * ) Notice: Subject to any disclaimer, the term of this patent is extended or adjusted under 35 U.S.C. 154(b) by 0 days.

(21) Appl. No.: 16/359,126

(22) Filed: Mar. 20, 2019

(65) Prior Publication Data

US 2019/0294843 A1 Sep. 26, 2019

Related U.S. Application Data

(60) Provisional application No. 62/646,848, filed on Mar. 22, 2018.

(51) Int. Cl.
*G06K 7/14* (2006.01)
*G06K 19/06* (2006.01)
*G16H 10/60* (2018.01)

(52) U.S. Cl.
CPC ..... *G06K 7/1417* (2013.01); *G06K 19/06037* (2013.01); *G16H 10/60* (2018.01)

(58) Field of Classification Search
CPC . G06K 7/1417; G06K 19/06037; G16H 10/60
See application file for complete search history.

(56) References Cited

U.S. PATENT DOCUMENTS

| | | | | |
|---|---|---|---|---|
| 2007/0136202 A1* | 6/2007 | Noma | ................... | G06Q 99/00 705/51 |
| 2010/0332257 A1* | 12/2010 | Sims | ..................... | G06Q 10/00 705/3 |
| 2013/0175334 A1* | 7/2013 | Miller | .................... | G16H 10/60 235/375 |
| 2013/0290013 A1* | 10/2013 | Forrester | ................ | G16H 40/63 705/2 |
| 2014/0070012 A1* | 3/2014 | Hunt | ................ | G06K 19/06037 235/494 |
| 2014/0095200 A1* | 4/2014 | Bostock | .................. | A61C 13/00 705/3 |
| 2019/0114365 A1* | 4/2019 | Liu | ........................ | G06F 16/958 |

* cited by examiner

*Primary Examiner* — Laura A Gudorf
(74) *Attorney, Agent, or Firm* — Andrew Morabito

(57) ABSTRACT

The present invention is a method for accessing medical information, the method comprising; receiving, by one or more processors, a first set of data, wherein the first set of data is associated with a user account, assigning, by one or more processors, a first code to the user account, wherein the code is readable by a code reading device, activating, by one or more processors, the first code, wherein the first set of data is connected to the first code, receiving, by one or more processors, confirmation that the first code is scanned by the code reading device, providing, by one or more processors, the first set of data to the code reading device, and collecting, by one or more processors, a second set of data from the code reading device.

12 Claims, 5 Drawing Sheets

METHOD AND SYSTEM FOR EMERGENCY DATA RETRIEVAL FROM TWO DIMENSIONAL CODE

CROSS-REFERENCE TO RELATED APPLICATIONS

This application is a continuation-in-part (and claims the benefit of priority under 35 USC 120) of U.S. application No. 62/646,848 filed Mar. 22, 2018. The disclosure of the prior applications is considered part of (and is incorporated by reference in) the disclosure of this application.

BACKGROUND

This disclosure relates generally medical information retrieval system, and more particularly to a method, computer program and computer system for storing medical data using quick response codes.

In the medical field, almost 100 million Americans have chronic conditions and millions more will develop them as America ages. Over 60 million Americans have a medical condition that should be known by medical professionals during treatment and/or in times of emergency. These medical conditions include allergies, chronic diseases, drug dependencies and genetic predispositions that can be critical during treatment and particularly in life or death situations. Studies show that accidents and medical emergencies can happen to anyone. Recent data reveals that 23% of emergency room admissions are injury or poisoning related. Another 15% are circulatory or respiratory.

If a medical emergency occurs, quick action can be important to saving lives and reduce permanent injury. If an ill or injured person and/or others with that person cannot obtain up-to-date care information rapidly, the lack of information can cause problems for effective treatment of the individual and potentially endanger the individual and/or delay treatment.

Studies have found that triage in the emergency ambulance service at times misses patients with life-threatening conditions. Emergency Medical Services (EMS) first responders are forced to make triage decisions based on limited available information and often under tremendous pressure such as in mass casualty scenarios. As a consequence, many people die or are disabled from heart attack, cardiac arrest, and stroke because they do not get lifesaving treatment in time.

Emergency room personnel and paramedics often spend a large amount of time acquiring pertinent background medical information for persons who are unable to convey such information themselves. For example, a person may be unconscious and lacking any personal identification and emergency contacts. Precious treatment time can be wasted tracking down background medical information. With emergency medical services, an important factor is not only how quickly paramedics arrive at the scene, but how quickly they can begin treatment. Another important factor using up precious time and raising insurance premiums, is the large number of unnecessary tests run to determine something that is already known about the person.

A barcode is an optical machine-readable representation of data, which shows data about the object to which it attaches. One-dimension 1D barcodes represented data by varying the widths and spacing of parallel lines. Later, barcodes evolved into two-dimension 2D, including rectangles, dots, hexagons, and other geometric patterns. Although 2D systems use a variety of symbols, they are generally referred to as barcodes as well. Barcodes are used to record and transmit data such as product identifiers. Advantageously, barcodes are computer readable, but are not directly readable by humans. As such, the data contained in a barcode is somewhat encrypted. A quick response code ("QR code") is a type of matrix 2D barcode. The QR code is one of the most popular types of 2D barcodes because it is designed to allow its contents to be decoded at high speed (i.e., fast readability) and QR codes provide relatively large storage capacity.

Therefore, it is desired for a method, computer program, or computer system provide vital medical information provided by the person in an encrypted display, so that medical professionals are able to quickly and easily access the information.

SUMMARY

In a first embodiment, the present invention is a method for accessing medical information, the method comprising: receiving, by one or more processors, a first set of data, wherein the first set of data is associated with a user account; assigning, by one or more processors, a first code to the user account, wherein the code is readable by a code reading device; activating, by one or more processors, the first code, wherein the first set of data is connected to the first code; receiving, by one or more processors, confirmation that the first code is scanned by the code reading device; providing, by one or more processors, a first portion of the first set of data to the code reading device; and collecting, by one or more processors, a second set of data from the code reading device.

In a second embodiment, the present invention is a computer program product for accessing medical information, the computer program product comprising: one or more computer readable storage media and program instructions stored on the one or more computer readable storage media, the program instructions comprising: computer instructions to receive a first set of data, wherein the first set of data is associated with a user account; computer instructions to assign a first code to the user account, wherein the code is readable by a code reading device; computer instructions to activate the first code, wherein the first set of data is connected to the first code; computer instructions to receive confirmation that the first code is scanned by the code reading device; computer instructions to provide a first portion of the first set of data to the code reading device; and computer instructions to collect a second set of data from the code reading device.

In a third embodiment, the present invention is a computer system for accessing medical information, the computer system comprising: one or more computer readable storage media and program instructions stored on the one or more computer readable storage media, the program instructions comprising: computer instructions to receive a first set of data, wherein the first set of data is associated with a user account; computer instructions to assign a first code to the user account, wherein the code is readable by a code reading device; computer instructions to activate the first code, wherein the first set of data is connected to the first code; computer instructions to receive confirmation that the first code is scanned by the code reading device; computer instructions to provide a first portion of the first set of data to the code reading device; and computer instructions to collect a second set of data from the code reading device.

DETAILED DESCRIPTION

Figure 1:
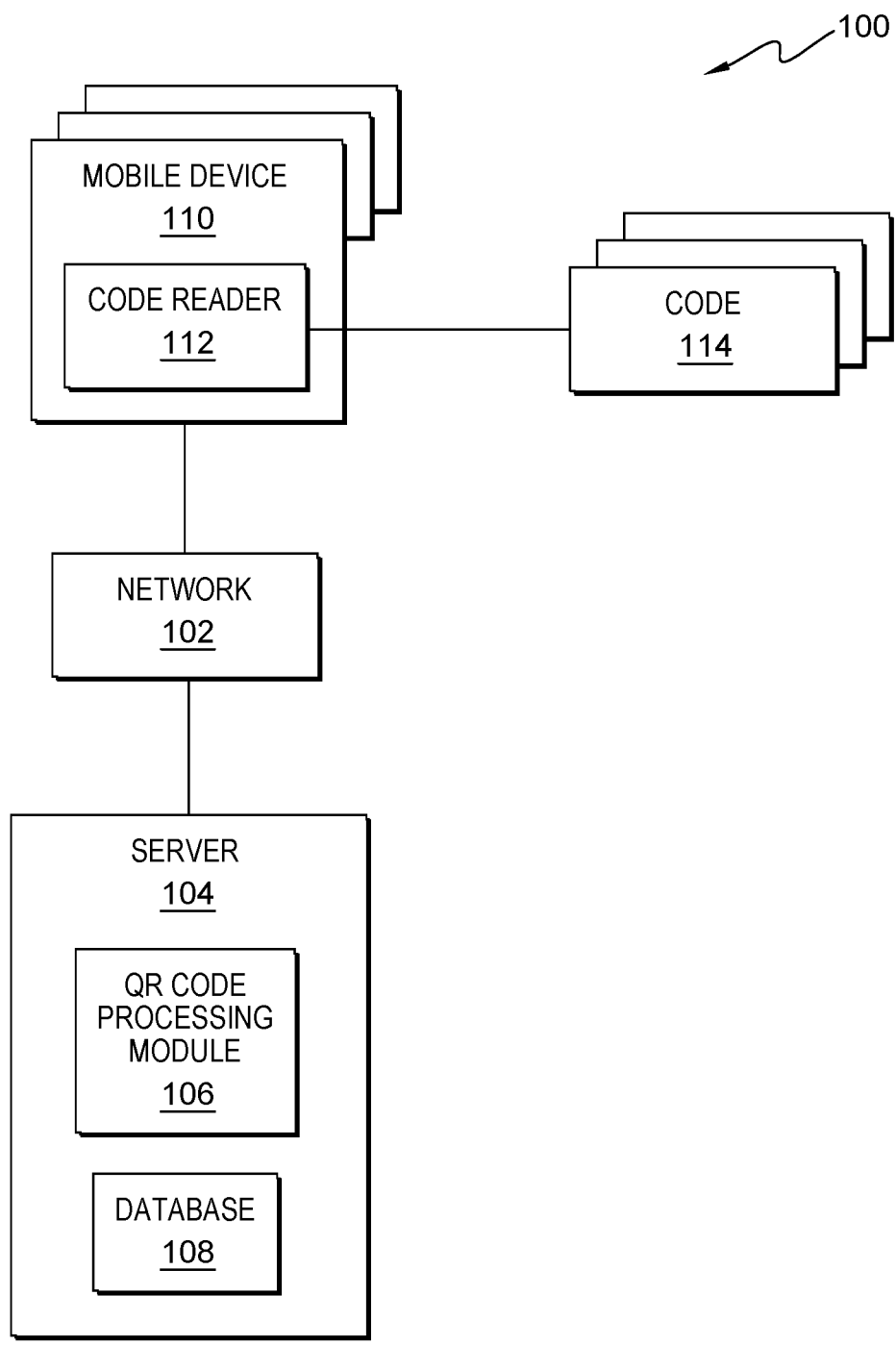
FIG. 1 depicts a block diagram depicting a computing environment, in accordance with one embodiment of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects may generally be referred to herein as a "circuit," "module", or "system." Furthermore, aspects of the present invention may take the form of a computer program product embodied in one or more computer readable medium(s) having computer readable program code/instructions embodied thereon.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Embodiments of the present invention discloses an approach to assist clients with their conditions in a safe and secure manner while also providing their providers with ample information to further assist the client gain control of their condition.

FIG. 1 depicts a block diagram of a computing environment 100 in accordance with one embodiment of the present invention. FIG. 1 provides an illustration of one embodiment and does not imply any limitations regarding the environment in which different embodiments maybe implemented.

In the depicted embodiment, computing environment 100 includes network 102, mobile computing devices 110, server 104, and election processing client 108. Computing environment 100 may include additional servers, computers, or other devices not shown.

Network 102 may be a local area network (LAN), a wide area network (WAN) such as the Internet, any combination thereof, or any combination of connections and protocols that can support communications between server 104 and mobile devices 110 in accordance with embodiments of the invention. Network 102 may include wired, wireless, or fiber optic connections.

Server 104 may be a management server, a web server, or any other electronic device or computing system capable of processing program instructions and receiving and sending data. In other embodiments server 104 may be a laptop computer, tablet computer, netbook computer, personal computer (PC), a desktop computer, or any programmable electronic device capable of communicating via network 102. In one embodiment, server 104 may be a server computing system utilizing multiple computers as a server system, such as in a cloud computing environment. In one embodiment, server 104 represents a computing system utilizing clustered computers and components to act as a single pool of seamless resources. In the depicted embodiment database 108 is located on server 104. Server 104 may include components, as depicted and described in further detail with respect to FIG. 5.

Database 108 may be a repository that may be written to and/or read by code processing module 106. Information gathered from the mobile device 110 associated with the code 114 may be stored to database 108. Such information may include previous scores, audio files, textual breakdowns, facts, events, and contact information. In one embodiment, database 108 is a database management system (DBMS) used to allow the definition, creation, querying, update, and administration of a database(s). In the depicted embodiment, database 108 resides on mobile computing devices 110. In other embodiments, database 108 resides on another server, or another computing device, provided that database 108 is accessible to code processing module 106.

Code processing module 106 operates to both associate the data with a code 114, as well as process the data stored in the code 114 when read. In the depicted embodiment, code processing module 106 utilizes network 102 to access the mobile devices 110 and the server 104 and communicates with database 108. In one embodiment, code processing module 106 resides on mobile computing devices 110. In other embodiments, code processing module 106 may be located on another server or computing device, provided code processing module 106 has access to database 108.

Mobile computing devices 110 may be management servers, a web servers, or any other electronic device or computing system capable of processing program instructions and receiving and sending data. In some embodiments, mobile computing devices 110 may be a smart phone, a mobile phone, a laptop computer, a tablet computer, a netbook computer, a personal computer (PC), a desktop computer, or any programmable electronic device capable of communicating with server 104 via network 102 and be able to communicate with or process information from code 114. In other embodiments, mobile computing devices 110 may represent a server computing system utilizing multiple computers as a server system, such as in a cloud computing environment. In another embodiment, mobile computing devices 110 represents a computing system utilizing clustered computers and components to act as a single pool of seamless resources. In the depicted embodiment, mobile computing devices 110 access voter identification information 103. This information may be state or federal identification cards (e.g. drivers licenses) or other forms of identification information which is able to verify a voter with the governing body with whom they are attempting to electronically submit a vote to. Mobile computing devices 110 may include components, as depicted and described in further detail with respect to FIG. 4.

The mobile device is equipped with a code reader 112. The code reader 112 is the hardware and/or software components of the mobile device 110 capable to scan the code 114, execute the QR code processing module 106, or receive the code 114 data. This may be in the form of an app or software which can scan and analyze the content of the code. The hardware element may be a camera or code specific reading device. In some embodiments, the code reader 112 is able to receive input information from the code 114 and process that. For example, inputting the code manually into the mobile computing device 110 and accessing the information stored in the code 114 via network 102.

Code 114 is the 1D or 2D optically machine-readable representation of data. The code 114 is readable by the mobile devices 110. The code 114 may be, a one-dimensional barcode or a two-dimensional barcode. This includes, but not limited to, including rectangles, dots, hexagons, and other geometric patterns. In some embodiments, the code is in the form of a quick response (QR). Various other types of codes can be used to replace the QR code format provided they are readable by the code reader 112 on the mobile devices 110.

The code 114 can be referred to as a QR code, medical QR code, code card, code sticker, code ID, code keychain, etc. The code 114 provides a unique identifier associated with the user that allows personnel to access person data quickly and easily. The code 114 conveys a link to the information stored in a remote server. The link allows the information to be accessed, over the web, without needing to know a username or password. The unique identifier corresponds to the user, such that one code 114 is uniquely assigned to one person.

In some embodiments, the code 114 has more than one code, wherein a first code access the user account and the second code accesses the service provider. The service provider provides an alternative mean to access to the information if the mobile computing device 110 is unable to communicate with code 114 directly.

Figure 2:
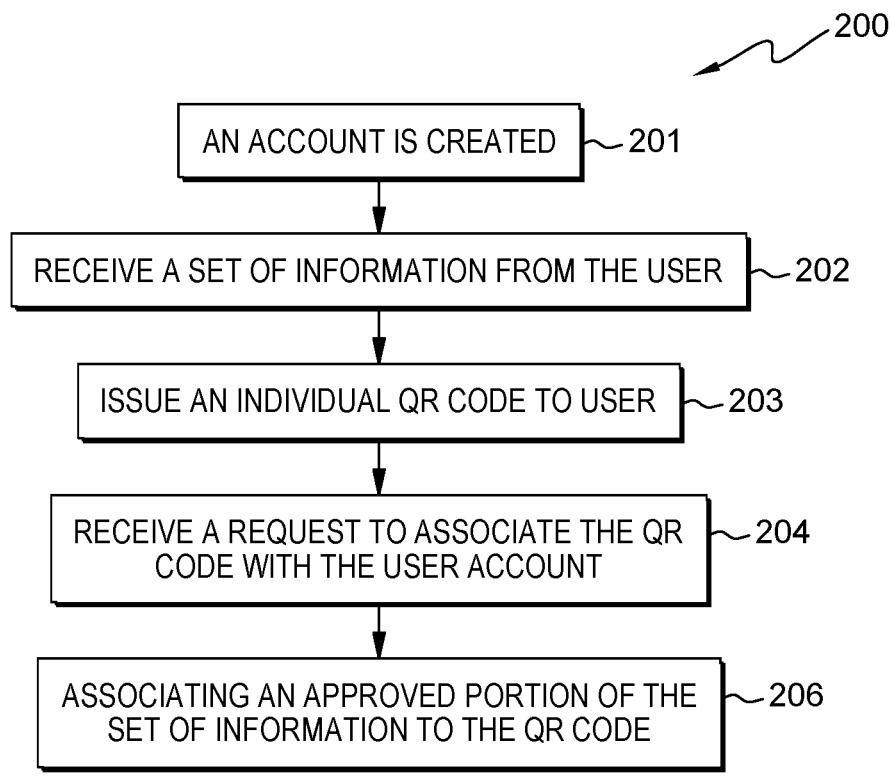
FIG. 2 depicts a flowchart of the operational steps taken by processing module to associate data with the code using a computing device within the computing environment of FIG. 1, in accordance with an embodiment of the present invention.

FIG. 2 depicts a flowchart of the operational steps taken by processing module to associate data with the code 114 using a computing device within the computing environment of FIG. 1, in accordance with an embodiment of the present invention.

A user first enrolls with the system and a user account is created 201. Once the user creates the account, the user submits any and all information which the user desires to have in their account. The user has the ability to provide information which the user is comfortable sharing and is not required to apply any specific information. The association of information and features of the account are at the user's discretion. In some embodiments, the user is able to activate additional features associated with their account such as emergency contacts, information which is provided to the emergency contacts, and the like.

Due to the information being supplied purely by the user and there is no requirement to release any specific medical records, informed that is supplied at the person's discretion and the website is not compliant with the Health Insurance Portability and Accountability Act of 1996 (HIPAA) Privacy and Security Rules. As the account does not require specific information, and the user is supplying the information at their own discretion.

The user may access the account through the mobile device or a website. The user may set a username and password to the account. Additional security techniques may be implemented, the identification of which is apparent to one of ordinary skill in the art, in order to ensure the user's privacy and secure nature of the information stored. The user is able to later modify, delete, or supply supplemental information to the account. This allows the user to freely once the account is created to update the information at anytime, regardless of the release of the code 114. Since the data is stored in a database and is not directly embedded in the code 114, the user is able to adjust the information in their account as they wish.

In one embodiment, the user is supplying important and relevant medical information which would be of great assistance to medical professionals in an emergency situation. The user would associate important medical information such as allegories, preexisting conditions, and the like which would be of great assistance to the medical professionals. The user, is likely to have difficulty communicating with medical personnel due to being unconscious, being an infant or minor, or a language barrier, or the user may also have difficulty accurately conveying his/her medical history because the wide breadth of information or due to a poor memory.

The processing module 106 associates (202) the information to the user account and stores the data in a database. In some embodiments, the information is stored in a Once the user supplied information is associated with the account and stored, the processing module 106 issues (203) an individual code 114 to the user's account. In some embodiments, the user may be assigned more than one code 114. The user then determines when to activate the code 114, wherein the activation of the code 114 by the user is received by the processing module 106 (204), the processing module 106 associates (206) the stored data with the code 114 which was activated. In some embodiments, the user is able to determine when the code 114 is active, how long it remains active for, what information is accessible through scanning the code 114, or the like.

Figure 3:
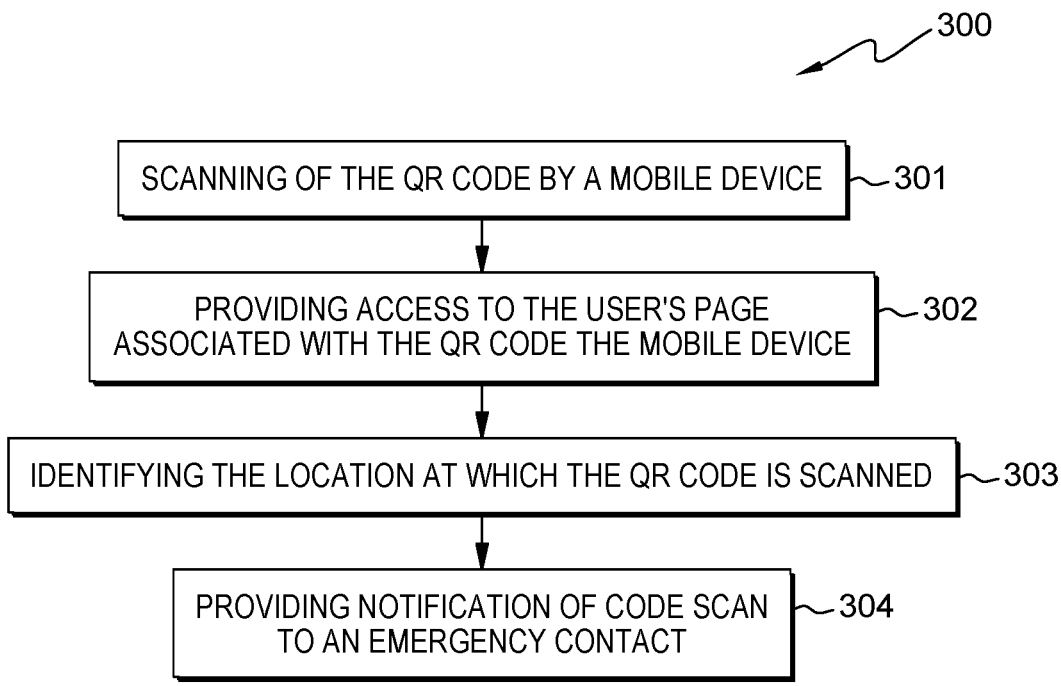
FIG. 3 depicts a flowchart of the operational steps taken by processing module to retrieve data associate with the code using a computing device within the computing environment of FIG. 1, in accordance with an embodiment of the present invention.

FIG. 3 depicts a flowchart of the operational steps taken by processing module to retrieve data associate with the code 114 using a computing device within the computing environment of FIG. 1, in accordance with an embodiment of the present invention.

Figure 4:
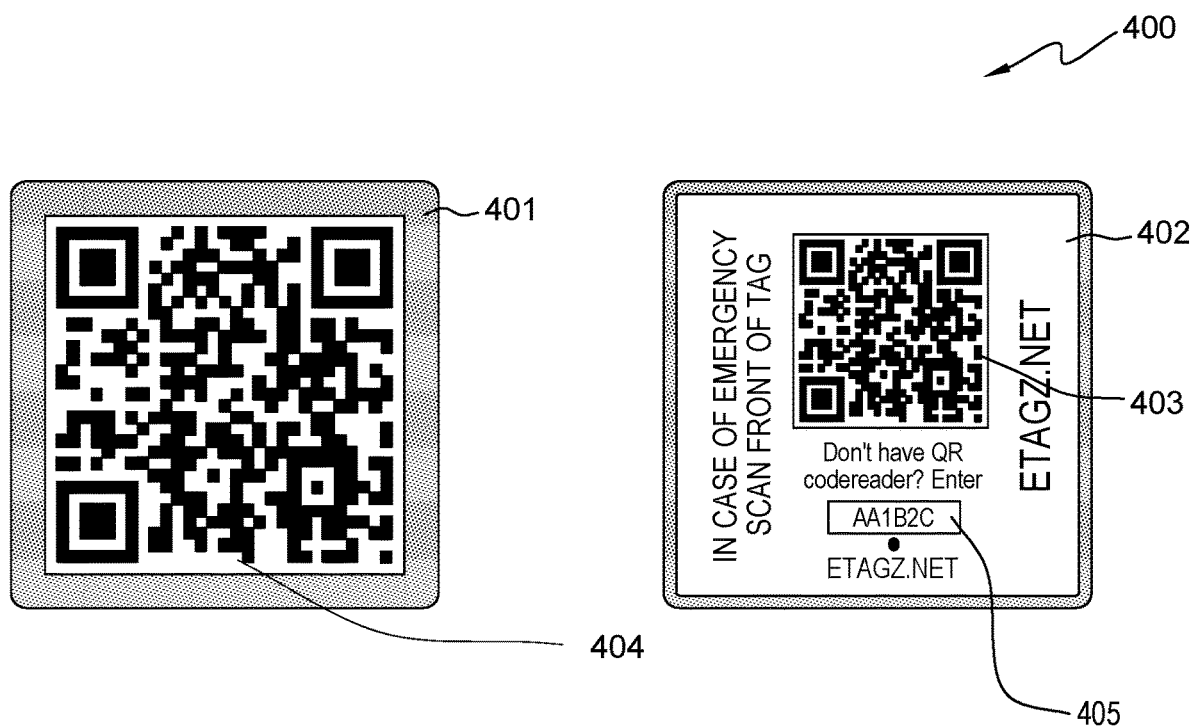
FIG. 4 depicts an illustration of a barcode, in accordance with one embodiment of the present invention.

Once the processing module 106 receives (301) notice that a code 114 has been scanned by a mobile device 110. The processing module 106 provides (302) a link, or direct access to the user's page which is stored and associated with the code 114. In some embodiments, the mobile device 110 may have an app which provides direct feed to the information. In additional embodiments, the mobile device 110 is provided a link, which need to be activated to connect to the server 104. In additional embodiments, the mobile device 110 is redirected to a webpage which requires the personnel to input a code which is next to or associated with the code 114 (FIG. 4). Upon the completion of the required scanning and inputting step, the processing module 106 presented on the mobile device 110 the non-restricted information associated with the user account.

In one embodiment, the code 114 is a visual code which the code reader 112 can decode into a URL. The URL points to a website running hypertext preprocessor (PHP). PHP is an HTML-embedded Scripting language with much of its syntax being borrowed from other programming languages (e.g., C. Java, Pert, etc.). The URL also contains the persons identifier and the key. Upon receiving the web request and before delivering any header information to the client, the web server looks up the key associated with the given person identifier in the database 108 and confirms that it matches the key passed in the URL. Once confirmed, the web server creates a temporary key for the given person and stores that pairing in the database 108. The temporary key expires after a predetermined time in the database and on the browser cookie.

In some embodiments, the processing module 106 provides the information for a predetermined time period and after that predetermined time period, the information disappears from the mobile device 110. The code 114 can be easily rescanned to repopulate the information, but as a security measure, the information cannot be booked mark or saved outside of the user account.

The processing module 106, identifies (303) the position/location of the code 114 when scanned. The position of the mobile device 110 is collected as the location of the code 114 when scanned. This information is stored in database 104. In additional to the location based on the global positioning system (GPS) or the like of the mobile device 110, the time, and other information (e.g. photo, audio, and the like which can be captured by the mobile device 110) relevant may be recorded as well.

The processing module 106 supplies (304) specific information to a separate mobile device 110, which is associated with the user account as either a subscriber or an emergency contact, which was decided by the user when supplying information for the account. This contact is provided with a predetermined amount of information which is determined by the user at the time of setting up the account. For example, the contact may receive a notice that the code 114 was scanned, at a specific time, at a specific location. In certain situations, where the user is a child or elderly person, the guardian of the user is able to quickly know that a situation has arisen, likely an emergency situation, where they can easily locate the user and find them. In some embodiments, the mobile device which scanned the code contact information is provided to the contact so they can get in direct communication with the personnel who scanned the code 114 to provide further information and get an understanding of the situation.

In another embodiment of the invention, the server may send an automated email or message alert that is sent to the contact and/or user that the code 114 has been scanned to mitigate identity fraud.

FIG. 4 depicts an illustration of a tag 400, in accordance with one embodiment of the present invention. In the depicted embodiment, the tag 400 is a two sided plate, where one side 401 is a first code 404 which is directly linked to the user account. The second side 402 provides additional means to access the user account. Through a general code 403 which directs the person to the service provider, wherein the person will then input a password 405. This provides the ability for the personnel to access the information in a variety of ways based on the mobile device 110 and the features of the device. For example, if the mobile device 110 has the application, the person can then scan code 404, directly linking the person to the user account. The person can also scan code 403 on side 402 to gain access to the service, and input the user password 405. Additionally, if the mobile device 110 either does not have or is not working, the side 402 provides the website address for the personnel to manually input in a different device which is connected to a network.

The program(s) described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Figure 5:
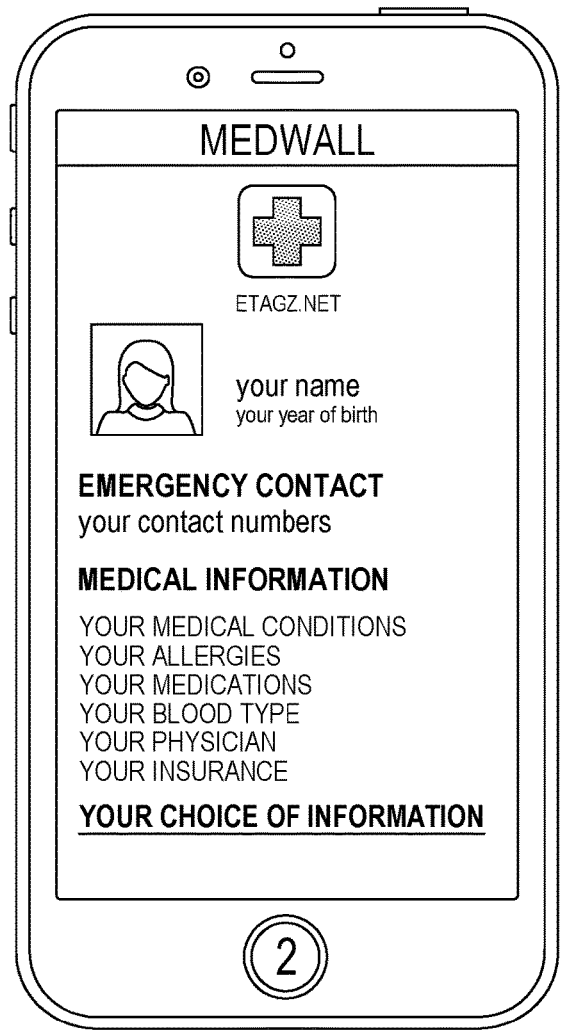
FIG. 5 depicts an illustration of a screen shot of the user page, in accordance with one embodiment of the present invention.

FIG. 5 depicts an illustration of the user's page 500, in accordance with one embodiment of the present invention. In the depicted embodiment, the code 114 is a two sided plate, where one side 401 is a code 114 which is directly linked to the user account. The user's page 500 can display the person's portrait, name, age, emergency contact and her phone number. The portrait verifies that the emergency personnel have the information for the correct person. The phone number listed is the person's emergency contact, Sometimes referred to as an in case of emergency (ICE) contact. The emergency contact and 911 are hot linked for ease of calling. The person's medical conditions, medication, dosages, frequency, recent surgeries, and medical devices. Medical conditions may include high blood pressure, diabetes, epilepsy, previous heart attacks, and strokes. The person's allergies, reactions, hospital preference, physician, and insurance information, or the like. Any information which the person wishes to have displayed when the code 114 is read, is accessible.

Figure 6:
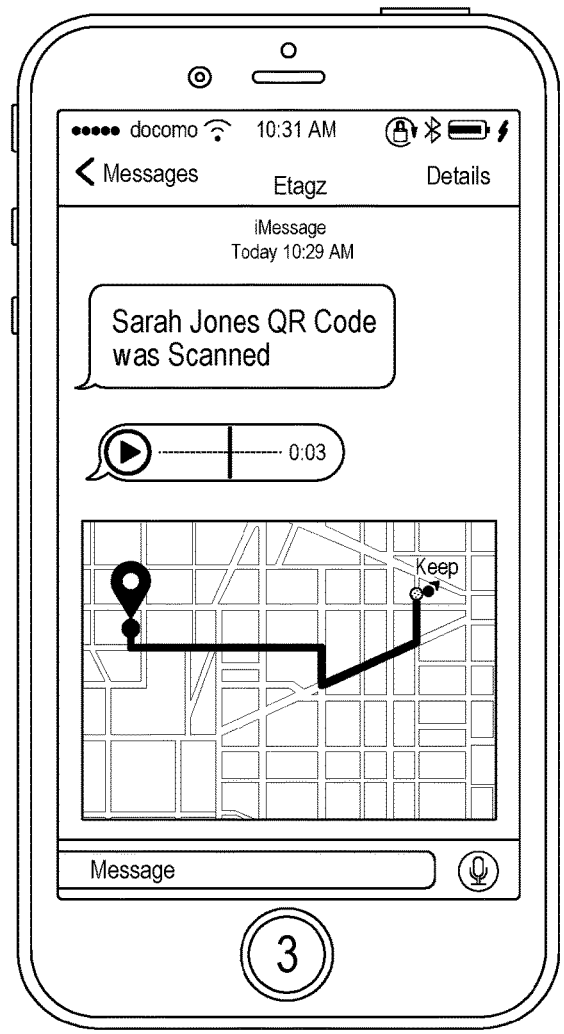
FIG. 6 depicts an illustration of a screen shot of the emergency contact notification(s), in accordance with one embodiment of the present invention.

FIG. 6 depicts an illustration of a screen shot 600 of an emergency contact's notification screen, in accordance with one embodiment of the present invention. In the depicted embodiment, the emergency contact is provided with a written notification 602, an audio file 604, and a location 606. The written notification 602 may be a message saying the code 114 was scanned, or may include additional information about the situation, which the mobile computing device 110 is able to collect from the situation. The audio file 604 may be a recording of what was accruing at the time of scanning the code 114, may be recorded by the person scanning the code 114 to let the emergency contact know of the situation, or the like. In some embodiments, the audio file 604 may be accompanied by a picture or video. The location notification 606 may also provide the fasted route to get to the location where the code 114 was scanned through third party services and knowledge of the emergency contact's location.

Figure 7:
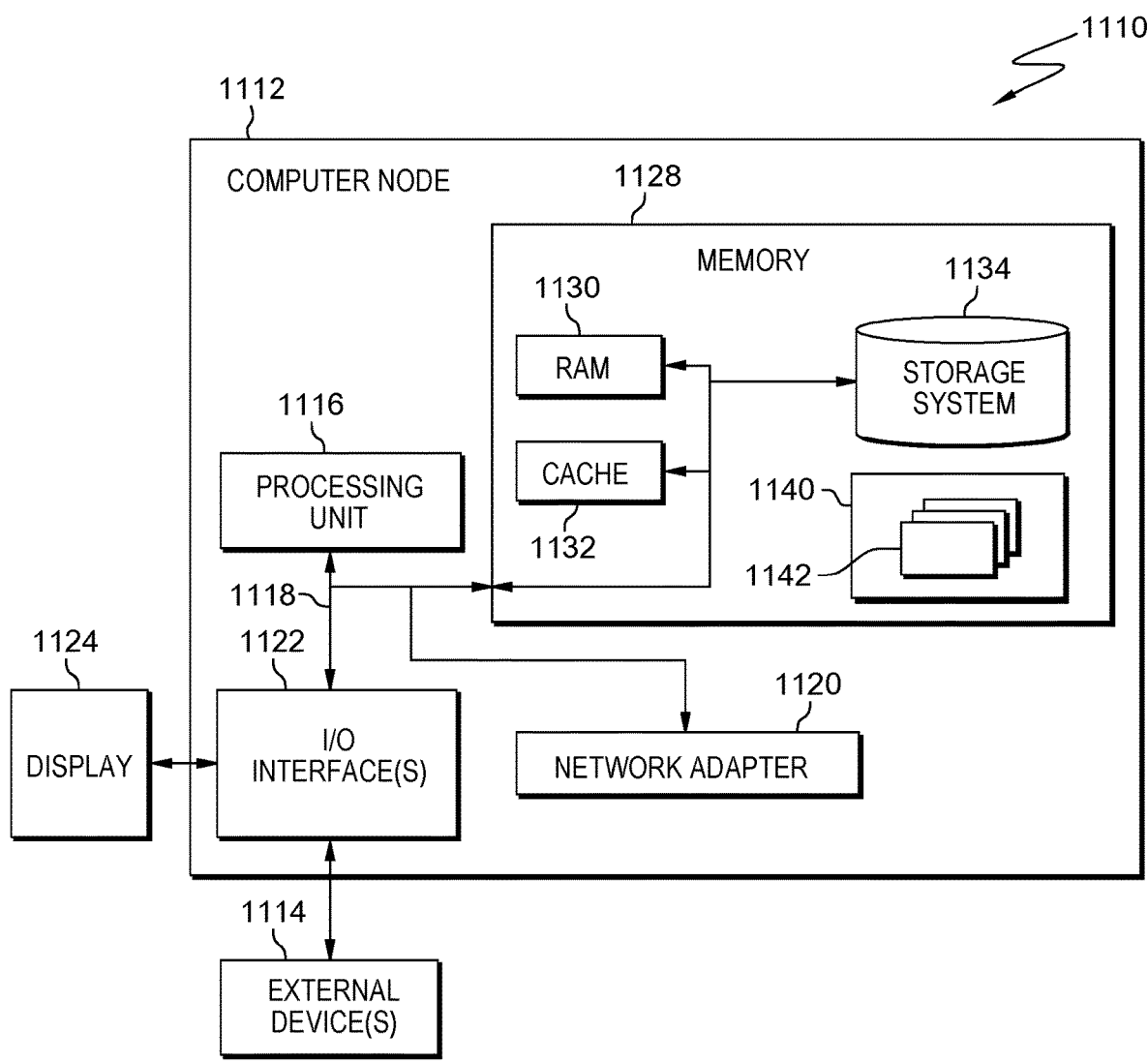
FIG. 7 depicts a block diagram depicting the internal and external components of the server of FIG. 1, in accordance with one embodiment of the present invention.

Referring now to FIG. 7, a schematic of an example of a computing node is shown. computing node 1110 is only one example of a suitable computing node and is not intended to suggest any limitation as to the scope of use or functionality of embodiments of the invention described herein. Regardless, computing node 1110 is capable of being implemented and/or performing any of the functionality set forth hereinabove.

In computing node 1110 there is a computer system/server 1112, which is operational with numerous other general purpose or special purpose computing system environments or configurations. Examples of well-known computing systems, environments, and/or configurations that may be suitable for use with computer system/server 1112 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed computing environments that include any of the above systems or devices, and the like.

Computer system/server 1112 may be described in the general context of computer system executable instructions, such as program modules, being executed by a computer system. Generally, program modules may include routines, programs, objects, components, logic, data structures, and so on that perform particular tasks or implement particular abstract data types. Computer system/server 1112 may be practiced in distributed computing environments where tasks are performed by remote processing devices that are linked through a communications network. In a distributed computing environment, program modules may be located in both local and remote computer system storage media including memory storage devices.

As shown in FIG. 5, computer system/server 1112 in computing node 1110 is shown in the form of a general-purpose computing device. The components of computer system/server 1112 may include, but are not limited to, one or more processors or processing units 1116, a system memory 1128, and a bus 1118 that couples various system components including system memory 1128 to processor 1116.

Bus 1118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1112 typically includes a variety of computer system readable media. Such media may be any available media that is accessible by computer system/server 1112, and it includes both volatile and non-volatile media, removable and non-removable media.

System memory 1128 can include computer system readable media in the form of volatile memory, such as random access memory (RAM) 1130 and/or cache memory 1132. Computer system/server 1112 may further include other removable/non-removable, volatile/non-volatile computer system storage media. By way of example only, storage system 1134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1118 by one or more data media interfaces. As will be further depicted and described below, memory 1128 may include at least one program product having a set (e.g., at least one) of program modules that are configured to carry out the functions of embodiments of the invention.

Program/utility 1140, having a set (at least one) of program modules 1142, may be stored in memory 1128 by way of example, and not limitation, as well as an operating system, one or more application programs, other program modules, and program data. Each of the operating system, one or more application programs, other program modules, and program data or some combination thereof, may include an implementation of a networking environment. Program modules 1142 generally carry out the functions and/or methodologies of embodiments of the invention as described herein.

Computer system/server 1112 may also communicate with one or more external devices 1114 such as a keyboard, a pointing device, a display 1124, etc.; one or more devices that enable a user to interact with computer system/server 1112; and/or any devices (e.g., network card, modem, etc.) that enable computer system/server 1112 to communicate with one or more other computing devices. Such communication can occur via Input/Output (I/O) interfaces 1122. Still yet, computer system/server 1112 can communicate with one or more networks such as a local area network (LAN), a general wide area network (WAN), and/or a public network (e.g., the Internet) via network adapter 1120. As depicted, network adapter 1120 communicates with the other components of computer system/server 1112 via bus 1118. It should be understood that although not shown, other hardware and/or software components could be used in conjunction with computer system/server 1112. Examples, include, but are not limited to: microcode, device drivers, redundant processing units, external disk drive arrays, RAID systems, tape drives, and data archival storage systems, etc.

In certain embodiments, the server computer 100 has the architecture of computing node 1110. In certain embodiments, the server computer 100 is part of a cloud environment. In certain alternative embodiments, the server computer 100 is not part of a cloud environment.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

The foregoing descriptions of various embodiments have been presented only for purposes of illustration and description. They are not intended to be exhaustive or to limit the present invention to the forms disclosed. Accordingly, many modifications and variations of the present invention are possible in light of the above teachings will be apparent to practitioners skilled in the art. Additionally, the above disclosure is not intended to limit the present invention. In the specification and claims the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g. attached, adhered, joined) are to be construed broadly and may include intermediate members between a connection of elements and relative movement between elements. As such, joinder references do not necessarily infer that two elements are directly connected and in fixed relation to each other. Moreover, network connection references are to be construed broadly and may include intermediate members or devices between network connections of elements. As such, network connection references do not necessarily infer that two elements are in direct communication with each other. In some instances, in methodologies directly or indirectly set forth herein, various steps and operations are described in one possible order of operation, but those skilled in the art will recognize that steps and operations may be rearranged, replaced or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements and/or substantial equivalents.

What is claimed is:

1. A method for accessing medical information, the method comprising:
   receiving, by one or more processors, a first set of data, wherein the first set of data is associated with a user account, and supplied by the user;
   assigning, by one or more processors, a first code to the user account, wherein the code is readable by a code reading device;
   activating, by one or more processors, the first code, wherein the first set of data is connected to the first code, where the first code is activated for a predetermined time period;
   receiving, by one or more processors, confirmation that the first code is scanned by the code reading device;
   accessing, by one or more processors, the first set of data and providing the set of data to the code reading device;
   collecting, by one or more processors, a second set of data from the code reading device wherein the second set of data includes a route from a second device to a location where the first code was scanned; and
   sending, by one or more processors, a portion of the second set of data to the second device indicating that the first code was scanned.

2. The method for accessing medical information of claim 1, wherein the notification that the first barcode was scanned is sent with a portion of the second set of data to a device, wherein device details are provided in the first set of data.

3. The method for accessing medical information of claim 1, wherein the second set of data includes at least one of a global position of where the first code was scanned, audio information collected by the code reading device during a predetermined time period after the first code is activated, visual information collected by the code reading device during a predetermined time period after the first code is scanned, and the time the first code was scanned.

4. The method for accessing medical information of claim 1, wherein when the first code is scanned by the code reading device, further comprising, requesting, by one or more processors, a second code be input to gain access to the first set of data.

5. A computer program product for accessing medical information, the computer program product comprising:
   one or more computer readable storage media and program instructions stored on the one or more computer readable storage media, the program instructions comprising:
   computer instructions to receive a first set of data, wherein the first set of data is associated with a user account;
   computer instructions to assign a first code and a second code to the user account, wherein the first code is readable by a code reading device;
   computer instructions to activate the first code, wherein the first set of data is connected to the first code for a predetermined time period;
   computer instructions to receive confirmation that the first code is scanned by the code reading device or the second code is input to the code reading device;
   computer instructions to access the first set of data and provide the first set of data to the code reading device for a predetermined time period;
   computer instructions to collect a second set of data from the code reading device, wherein the second set of data includes a route from a second device to a location where the first code was scanned; and
   computer instructions to provide the first set of data and the second set of data to the second device.

6. The computer program product for accessing medical information of claim 5, wherein when the confirmation that the first code is scanned, further comprising, computer instructions to send a notification to a second device.

7. The computer program product for accessing medical information of claim 5, wherein the second set of data includes global position of the first code and time of confirmation of the scanning of the first code.

8. The computer program product for accessing medical information of claim 5, further comprising, computer instructions to deny access of the code reading device to the first set of data after a predetermined time of the confirmation of the first code being scanned.

9. The computer program product for accessing medical information of claim 5, wherein if the scanning of the first code fails, program instructions to input the second code.

10. The computer program product for accessing medical information of claim 5, wherein upon the scanning of the first code by the code reading device, program instructions to collect the second set of data from the code reading device, wherein the second set of data includes at least one of location information of the code reading device, and audio or visual data collectable by the code reading device.

11. A computer system for accessing medical information, the computer system comprising: one or more computer readable storage media and program instructions stored on the one or more computer readable storage media, the program instructions comprising:

computer instructions to receive a first set of data, wherein the first set of data is associated with a user account;

computer instructions to assign a first code to the user account, wherein the first code is readable by a code reading device;

computer instructions to activate the first code upon a set of requirements, wherein the first set of data is connected to the first code for a predetermined time period;

computer instructions to receive confirmation that the first code is scanned by the code reading device; computer instructions to provide the first set of data to the code reading device;

computer instructions to collect a second set of data from the code reading device at a time of scanning the first code wherein the second set of data includes a route from a second device to a location where the first code was scanned; and computer instructions to send a notification and a portion of the first set of data and the second set of data to the second device.

12. The computer system for accessing medical information of claim 11, wherein the second set of data includes global position of the first code and time of confirmation of the scanning of the first code.

* * * * *